US012758148B2

(12) United States Patent
Cha et al.

(10) Patent No.: US 12,758,148 B2
(45) Date of Patent: Oct. 13, 2026

(54) USER CLUSTERING AND ANALYSIS METHOD USING BODY COMPOSITION BIG DATA, AND SYSTEM THEREOF

(71) Applicant: InBodyHealthcare Co., Ltd., Seoul (KR)

(72) Inventors: Ki Chul Cha, Seoul (KR); Won Young Jang, Gyeonggi-do (KR); Soo Cheol Lim, Seoul (KR)

(73) Assignee: INBODYHEALTHCARE CO., LTD.

(*) Notice: Subject to any disclaimer, the term of this patent is extended or adjusted under 35 U.S.C. 154(b) by 379 days.

(21) Appl. No.: 18/198,741

(22) Filed: May 17, 2023

(65) Prior Publication Data

US 2023/0371891 A1 Nov. 23, 2023

(30) Foreign Application Priority Data

May 18, 2022 (KR) ........................ 10-2022-0060574
Jul. 22, 2022 (KR) ........................ 10-2022-0091253

(51) Int. Cl.
*A61B 5/00* (2006.01)

(52) U.S. Cl.
CPC .......... *A61B 5/4872* (2013.01); *A61B 5/7264* (2013.01); *A61B 5/742* (2013.01)

(58) Field of Classification Search
CPC ..... A61B 5/4872; A61B 5/7264; A61B 5/742; G16H 10/20
See application file for complete search history.

(56) References Cited

U.S. PATENT DOCUMENTS

2014/0025346 A1* 1/2014 Uchiyama ............ A61B 5/1072 703/1
2022/0076818 A1* 3/2022 Kodama .............. A61B 5/4872
2022/0076820 A1* 3/2022 Cha ........................ G16H 50/30

FOREIGN PATENT DOCUMENTS

KR 20130027187 A * 3/2013 ............. G01G 19/50

* cited by examiner

*Primary Examiner* — John R Downey
(74) *Attorney, Agent, or Firm* — MARSHALL, GERSTEIN & BORUN LLP

(57) ABSTRACT

A user clustering and analysis method using body composition big data and a system includes analyzing, by a body composition analyzer, a user's body composition, and transmitting analyzed body composition data of the user to a user terminal, receiving, by the user terminal, the user's body composition data, and transmitting the body composition data to a service provider server providing services related to body composition analysis or executing a body composition data analysis application thereof, and analyzing, by the service provider server or the body composition data analysis application of the user terminal, the user's body composition data accumulated for a predetermined period of time, assigning a cluster that is a group of similar body composition, and providing the cluster to the user terminal or displaying the cluster on a display screen.

10 Claims, 17 Drawing Sheets

100

USER CLUSTERING AND ANALYSIS METHOD USING BODY COMPOSITION BIG DATA, AND SYSTEM THEREOF

CROSS REFERENCE TO RELATED APPLICATIONS

The present application claims priority to Korean Patent Application Nos. 10-2022-0060574, filed May 18, 2022, and 10-2022-0091253, filed Jul. 22, 2022, the entire contents of which is incorporated herein for all purposes by this reference.

BACKGROUND OF THE INVENTION

Field of the Invention

The present disclosure relates to a user clustering and analysis method using body composition big data and a system thereof and, more particularly, to a user clustering and analysis method using body composition big data and a system thereof capable of providing users further improved body composition analysis services by explaining in detail user's body composition test results through artificial intelligence natural language processing deep learning.

Description of the Related Art

Recently, as modern people spend more time sitting, while studying, working, or the like in a limited space, the amount of exercise due to body activity has significantly decreased, and thus people are experiencing many problems due to obesity, muscle strength reduction, etc., which are caused by the decreased exercise.

In this regard, as the concerns about health and the awareness of need for exercise increase due to the problems such as obesity, muscle strength reduction, and the like, more and more people are trying to improve their physical strength and muscle strength through the exercises regardless of their gender and age. As part of these efforts, the number of people who exercise using various exercise equipment or programs after registering at a fitness center near their home or work is also on the rise. However, it is by no means an easy task to go to the fitness center and exercise regularly due to complex life patterns and the busy working life of modern people.

In modern society, interest in health is steadily increasing, and many people have a strong desire to frequently diagnose their physical conditions.

Conventionally, mere diagnosis and treatment in which an expert interprets measurement results of biological markers such as blood pressure, blood flow, and blood sugar, which are obtained by measurement devices, have been mainly performed, but in recent years, telemedicine in which the measurement results are transmitted by using communication technology is also becoming available. However, there are many difficulties for non-professional public to easily understand the results of medical measurements and determine their physical conditions. In addition, conventionally, a method of filling out a questionnaire used in medical consultation has not been unified, so the interpretation and evaluation of the questionnaire are often inconsistent.

Accordingly, there are desperate needs for a system or a solution by which users may easily measure (i.e., test) their own body composition through a body composition analyzer having a simple structured at home or at work, and receive more precise and diverse analysis services for their own body composition measurement (i.e., test) data.

SUMMARY OF THE INVENTION

The present disclosure has devised in comprehensive consideration of the matter described above, and an objective of the present disclosure is to provide a user clustering and analysis method using body composition big data and a system thereof that may provide more improved body composition analysis services to a user by providing a detailed explanation of user's body composition test results through artificial intelligence natural language processing deep learning enabling the services as if a health trainer were explaining the test results in detail whenever the user examines his or her body composition by using a body composition analyzer.

According to the present disclosure in order to achieve the above objectives, there is provided a user clustering and analysis method using body composition big data, the method including: a) analyzing, by a body composition analyzer, a user's body composition as the user uses the body composition analyzer to test his or her body composition, and transmitting analyzed body composition data of the user to a user terminal; b) receiving, by the user terminal, the user's body composition data from the body composition analyzer, and transmitting the body composition data to a service provider server providing services related to body composition analysis, or executing a body composition data analysis application installed in the user terminal; and c) receiving, by the service provider server, the user's body composition data through the user terminal, analyzing the user's body composition data accumulated for a predetermined period of time, assigning a cluster that is a group of similar body composition, and providing the cluster to the user terminal, or analyzing, by the user terminal, the user's body composition data accumulated for the predetermined period of time by execution of the body composition data analysis application, assigning the cluster that is the group of the similar body composition, and displaying the cluster on a display screen.

Here, in step c), when the service provider server analyzes the user's body composition data, assigns the cluster, which is the group of the similar body composition, and provides the cluster to the user terminal, or the user terminal analyzes the user's body composition data by execution of the body composition data analysis application, assigns the cluster that is the group of the similar body composition, and displays the cluster on the display screen, a description of the assigned cluster is provided.

In this case, in providing of the description of the assigned cluster, a description according to a cluster template that is set in advance in response to the cluster assigned to the user (i.e., an examinee) may be provided.

Here, in the template, a cluster name of the examinee, an illustration of the cluster, a one-line description expressing the cluster, a description of a naming reason for the cluster name, a position and description of the examinee in a big data map corresponding to age and gender of the examinee, a description of a percentile of the body composition of the examinee, a histogram description, and the like may be provided.

In this case, in addition, the service provider server or the body composition data analysis application may assign a specific name to each assigned cluster.

In this case, in addition, the service provider server or the body composition data analysis application may provide an illustration corresponding to each assigned specific name.

In this case, in addition, the service provider server or the body composition data analysis application may provide position information of the user on the big data in relation to the assigned cluster.

In addition, when the service provider server analyzes the user's body composition data, assigns the cluster, which is the group of the similar body composition, and provides the cluster to the user terminal, or the user terminal analyzes the user's body composition data by the execution of the body composition data analysis application, assigns the cluster that is the group of the similar body composition, and displays the cluster on the display screen, a description for a naming reason for the name assigned to each cluster may be provided.

In this case, the service provider server or the body composition data analysis application may provide information about that the cluster assigned to the user is a cluster corresponding to what percentage (%) of all examinees.

In this case, in addition, the service provider server or the body composition data analysis application may provide a percentile graph of the user on the big data.

In this case, in addition, the service provider server or the body composition data analysis application may provide an image storage function in a form of a card in which an illustration and a name are combined with each other.

In addition, in step c) of analyzing the user's body composition data by the service provider server or the body composition data analysis application installed the user terminal, the body composition big data of a group of at least one among a same country, gender, and age as those of the user (i.e., the examinee) may be extracted to generate a big data map, and then analysis may be performed on how much respective levels of at least one of obesity, muscle mass amount, and sarcopenia are illustrated in the group according to which coordinates the body composition data of the user (i.e., the examinee) is positioned in the generated body composition big data map.

In addition, in step c) of analyzing the user's body composition data and assigning the cluster, which is the group of the similar body composition, by the service provider server or the body composition data analysis application installed the user terminal, a predetermined statistically significant Body Mass Index (BMI) section may be divided into a plurality of stages on the body composition big data for each user's gender/age by country, a predetermined portion of a Percentage Body Fat (PBF) from total body composition big data included in a divided BMI band may be further divided into a plurality of regions, a cluster classification map that is changed depending on data parameters of each gender and each age group and has continuity may be generated, a map to be matched through age/gender information of the user who has completed a body composition test may be retrieved from a database (DB) to find a percentile position of each body composition of weight, height, body fat mass, and skeletal muscle mass and locate the percentile position on the map, and then the cluster may be assigned by a method of assigning one of a plurality of clusters on the basis of a unique address of a coordinate region to which the user (i.e., the examinee) belongs.

In this case, the section, from BMI 10 to BMI 42, statistically significant on the body composition big data for each user's gender/age by country may be divided into 60 stages.

In this case, in addition, an upper 1% to 99% of the PBF among the total body composition big data included in the divided BMI band may be further divided into nine regions by drawing lines.

In addition, according to the present disclosure in order to achieve the above objectives, there is provided a user clustering and analysis system using body composition big data, the system including: a body composition analyzer configured to analyze a user's body composition as the user uses the body composition analyzer to test his or her body composition, and transmit analyzed body composition data of the user to a user terminal; the user terminal configured to receive the user's body composition data from the body composition analyzer, and transmit the body composition data to a service provider server providing services related to body composition analysis, or configured to execute a body composition data analysis application installed in the user terminal, analyze the user's body composition data, assign a cluster that is a group of similar body composition, and display the cluster on a display screen; and the service provider server configured to receive, the user's body composition data through the user terminal, analyze the user's body composition data accumulated for a predetermined period of time, assign the cluster that is the group of the similar body composition, and provide the cluster to the user terminal.

Here, when the service provider server analyzes the user's body composition data, assigns the cluster, which is the group of the similar body composition, and provides the cluster to the user terminal, or the user terminal analyzes the user's body composition data by execution of the body composition data analysis application, assigns the cluster that is the group of the similar body composition, and displays the cluster on the display screen, a description of the assigned cluster may be provided.

In this case, in providing of the description of the assigned cluster, a description according to a cluster template that is set in advance in response to the cluster assigned to the user (i.e., the examinee) may be provided.

Here, in the template, a cluster name of the examinee, an illustration of the cluster, a one-line description expressing the cluster, a description of a naming reason for the cluster name, a position and description of the examinee in a big data map corresponding to age and gender of the examinee, a description of a percentile of the body composition of the examinee, a histogram description, and the like may be provided.

In this case, in addition, the service provider server or the body composition data analysis application may assign a specific name to each assigned cluster.

In this case, in addition, the service provider server or the body composition data analysis application may provide an illustration corresponding to each assigned specific name.

In this case, in addition, the service provider server or the body composition data analysis application may provide position information of the user on the big data in relation to the assigned cluster.

In addition, when the service provider server analyzes the user's body composition data, assigns the cluster, which is the group of the similar body composition, and provides the cluster to the user terminal or the user terminal analyzes the user's body composition data by the execution of the body composition data analysis application, assigns the cluster that is the group of the similar body composition, and displays the cluster on the display screen, the description for a naming reason for the name assigned to each cluster may be provided.

In this case, the service provider server or the body composition data analysis application may provide information about that the cluster assigned to the user is the cluster corresponding to what percentage (%) of all examinees.

In this case, in addition, the service provider server or the body composition data analysis application may provide a percentile graph of the user on the big data.

In this case, in addition, the service provider server or the body composition data analysis application may provide an image storage function in a form of a card in which an illustration and a name are combined with each other.

In addition, when the service provider server or the body composition data analysis application installed in the user terminal analyzes the user's body composition data, the body composition big data of a group of at least one among a same country, gender, and age as those of the user (i.e., the examinee) may be extracted to generate a big data map, and then analysis may be performed on how much respective levels of at least one of obesity, muscle mass amount, and sarcopenia are illustrated in the group according to which coordinates the body composition data of the user (i.e., the examinee) is positioned in the generated body composition big data map.

In addition, when the service provider server or the body composition data analysis application installed in the user terminal analyzes the user's body composition data and assigns the cluster, which is the group of the similar body composition, a predetermined statistically significant Body Mass Index (BMI) section may be divided into a plurality of stages on the body composition big data for each user's gender/age by country, a predetermined portion of a Percentage Body Fat (PBF) from the total body composition big data included in divided BMI band may be further divided into a plurality of regions, a cluster classification map that is changed depending on data parameters of each gender and each age group and has continuity may be generated, a map to be matched through age/gender information of the user who has completed a body composition test may be retrieved from a database (DB) to find a percentile position of each body composition of weight, height, body fat mass, and skeletal muscle mass and locate the percentile position on the map, and then the cluster may be assigned by a method of assigning one of a plurality of clusters on the basis of a unique address of a coordinate region to which the user (i.e., the examinee) belongs.

In this case, the section, from BMI 10 to BMI 42, statistically significant on the body composition big data for each user's gender/age by country may be divided into 60 stages.

In this case, in addition, an upper 1% to 99% of the PBF among the total body composition big data included in the divided BMI band may be further divided into nine regions by drawing lines.

In addition, the user terminal may be loaded with a specific health application, which is provided by the service provider server and configured to have functions of interworking with the body composition analyzer, allowing the user to view various body composition analysis results, and accumulating and recording changes in body composition.

In addition, the service provider server is provided with built-in databases, including: a member information DB configured to store information about service provider's health members subscribed to their memberships in order to receive various services provided by the service provider; a body composition DB configured to store body composition data of all users; a cluster DB configured to store final data of BMI and PBF required for cluster definition, and at the same time, record cumulative test results of the user (i.e., the examinee) in a big data DB; and the big data DB configured to provide information (i.e., data) to update the cluster DB on the basis of changed big data to the cluster DB.

In addition, the service provider server may be loaded with a one-month body composition analysis algorithm, which is a kind of software program, realized to use the body composition data of the user (i.e., the examinee) for one month and calculate the BMI and PBF, which are required for cluster definition.

According to the present disclosure as described above, there is provided an advantage that the more improved body composition analysis services may be provided to the user by providing the detailed explanation of the user's body composition test results through the artificial intelligence natural language processing deep learning enabling the services as if a health trainer were explaining the test results in detail whenever the user examines his or her body composition by using the body composition analyzer.

DETAILED DESCRIPTION OF THE DRAWINGS

The terms or words used in this description and claims are not to be construed as being limited to their ordinary or dictionary meanings, and should be interpreted as meanings and concepts corresponding to the technical spirit of the present invention based on the principle that inventors may properly define the concept of a term in order to best describe their invention.

Throughout the description of the present disclosure, when a part is said to "include" or "comprise" a certain component, it means that it may further include or comprise other components, except to exclude other components unless the context clearly indicates otherwise. In addition, the terms "~ part", "~ unit", "module", and the like mean a unit for processing at least one function or operation and may be implemented by a combination of hardware and/or software.

Hereinafter, an exemplary embodiment of the present disclosure will be described in detail with reference to the accompanying drawings.

Figure 1:
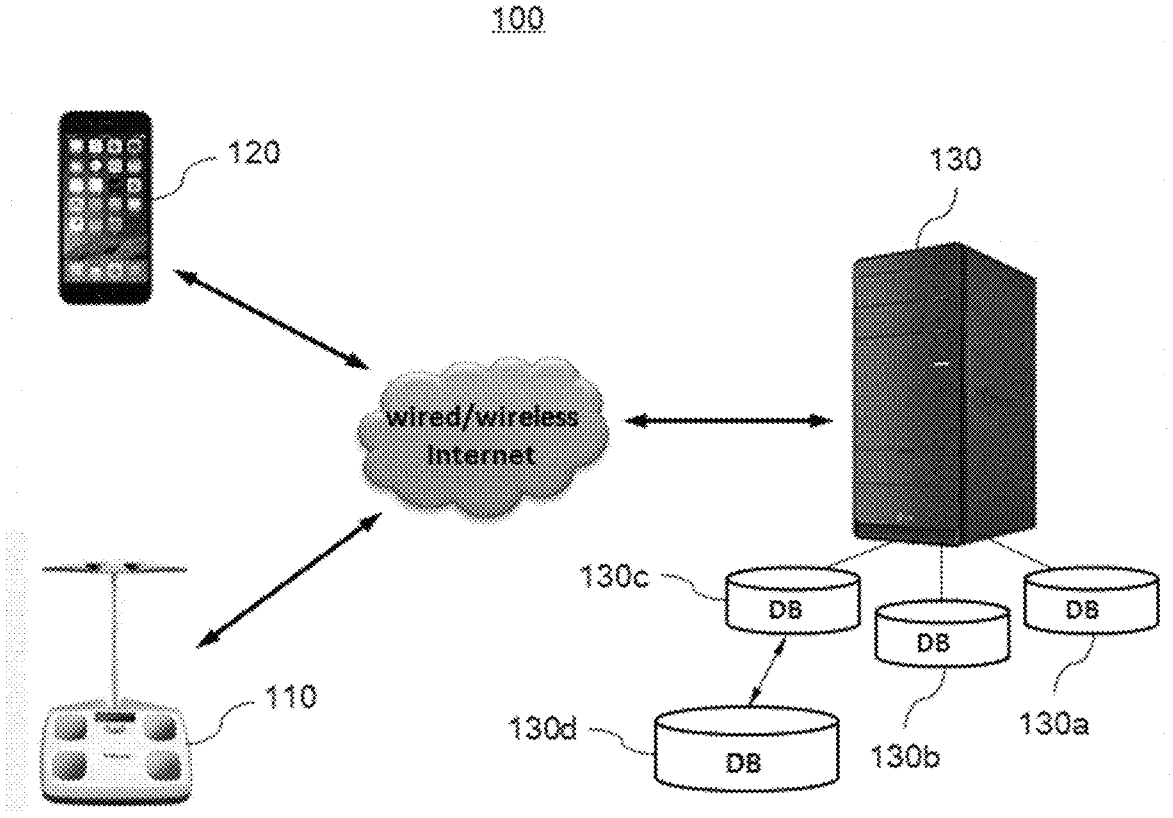
FIG. 1 is a view schematically illustrating a configuration of a user clustering and analysis system using body composition big data according to the present disclosure.

FIG. 1 is a view schematically illustrating a configuration of a user clustering and analysis system using body composition big data according to the exemplary embodiment of the present disclosure.

Referring to FIG. 1, the user clustering and analysis system 100 using the body composition big data according to the present disclosure is configured to include a body composition analyzer 110, a user terminal 120, and a service provider server 130.

As a user uses a device (i.e., the body composition analyzer 110) to test his or her body composition, the body composition analyzer 110 analyzes the user's body composition and transmits the user's analyzed body composition data to the user terminal 120. Here, more description will be added in relation to such a body composition analyzer 110.

Figure 2A:
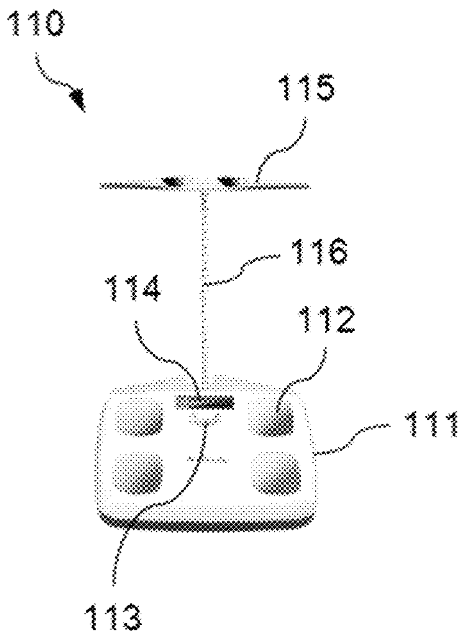
FIGS. 2A, 2B, and 2C are views illustrating a body composition analyzer applied to the system of the present disclosure and a use case thereof.
Figure 2B:
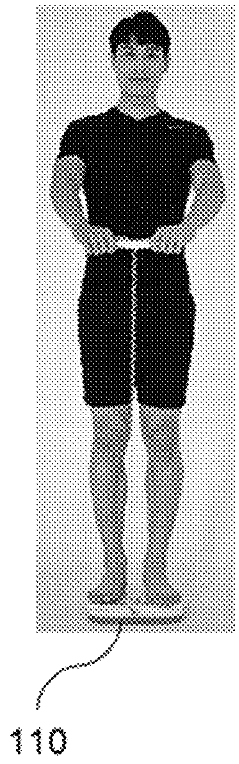
Figure 2C:
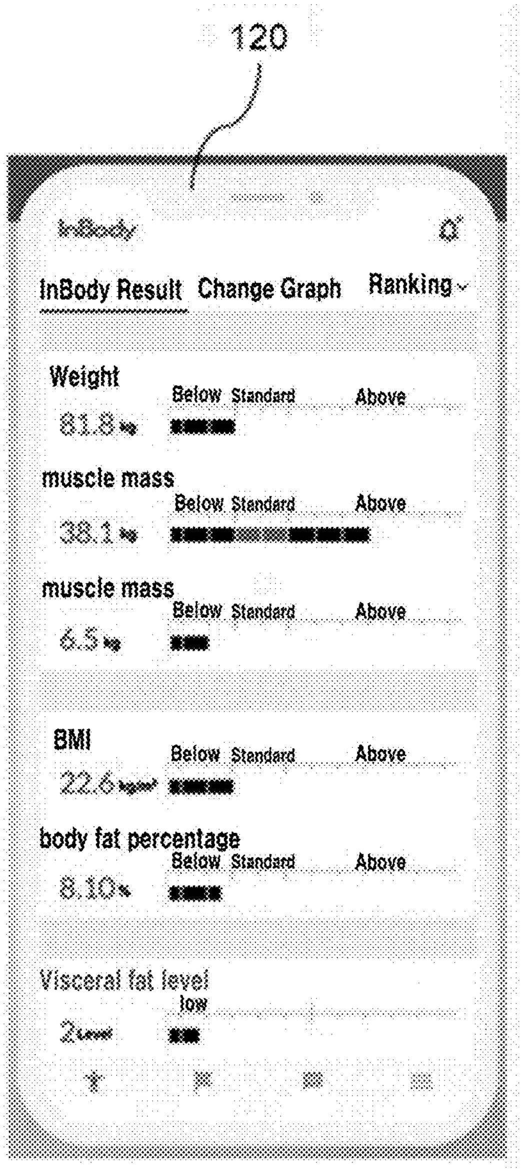

FIGS. 2A, 2B, and 2C are views illustrating the body composition analyzer applied to the system of the present disclosure and the use case thereof.

Referring to FIG. 2A, the body composition analyzer 110 is configured to include: a main body unit 111 configured to serve as a part constituting a main body of the body composition analyzer, and provided with an algorithm circuit unit related to body composition analysis and a wireless communication module for wireless communication with a user terminal 120, which are installed therein; a sensor unit 112 provided on an upper surface of the main body unit 111 to serve as a footrest on which a user (i.e., an examinee) stands on both feet as shown in FIG. 2B when the user uses the body composition analyzer 110, and provided with a high-sensitivity electrode sensor and an automatic zero-point compensation load cell, which are installed therein; a dial 113 configured to allow the user (i.e., the examinee) to input his or her height by turning the dial; a display unit 114 configured to display the height, a weight, a body fat percentage, muscle mass, a visceral fat level, and the like of the user (i.e., an examinee) through a LCD display window; a handle unit 115 provided with a pair of thumb electrodes for contacting both thumbs of the user (i.e., an examinee); and a connection unit 116 configured to mechanically and electrically connect the main body unit 111 and the handle unit 115 to each other.

Meanwhile, the user terminal 120 receives the user's body composition data (i.e., the muscle mass, body fat mass, BMI, body fat percentage, visceral fat level, and the like) transmitted from the body composition analyzer 110 as shown in FIG. 2C and transmits the user's body composition data to the service provider server 130 providing services related to body composition analysis, or executes the body composition data analysis application installed therein, analyzes the user's body composition data, assigns the cluster that is the group of the similar body composition, and displays the cluster on the display screen. Here, such a body composition data analysis application may be configured to be provided by the service provider server 130 described later, and the user terminal 120 downloads the application and stores the application in a memory thereof, thereby being installed in the user terminal 120.

Here, in addition, the user terminal 120 as described above may be loaded with a specific health application, which is provided by the service provider server 130 and having functions of interworking with the body composition analyzer 110, allowing a user to view various body composition analysis results, and accumulating and recording changes in body composition.

The service provider server 130 receives the user's body composition data through the user terminal 120, analyzes the user's body composition data accumulated for a predetermined period of time, assigns a cluster, which is a group of similar body composition, and provides the cluster to the user terminal 120. Here, such a service provider server 130 may be provided with built-in databases, including: a member information DB 130*a* configured to store information about service provider's health members subscribed to their memberships in order to receive various services (e.g., various services including various indicators related to body composition data analysis, health-related information, etc.) provided by the service provider; a body composition DB 130*b* configured to store body composition data of all users; a cluster DB 130*c* configured to store final data of BMI and PBF required for cluster definition, and at the same time, record cumulative test results of a user (i.e., an examinee) in a big data DB 130*d*; and the big data DB 130*d* configured to provide information (i.e., data) to update the cluster DB 130*c* on the basis of changed big data to the cluster DB 130*c*. In addition, the service provider server 130 may be loaded with a one-month body composition analysis algorithm, which is a kind of software program, realized to use the body composition data of the user (i.e., the examinee) for one month and calculate the BMI and PBF, which are required for cluster definition. Here, as described above, the service provider server 130 for analyzing the body composition data, assigning the cluster, and providing a description of the assigned cluster will be described again later.

Here, in addition, when the service provider server 130 analyzes the user's body composition data, assigns a cluster that is a group of similar body composition, and provides the cluster to the user terminal 120 or the user terminal 120 analyzes the user's body composition data by the execution of the body composition data analysis application, assigns the cluster that is the group of the similar body composition, and displays the cluster on the display screen, a description of the assigned cluster may be provided.

In this case, in providing the description of the assigned cluster, a description related to a cluster template that is set in advance in response to the cluster assigned to the user (i.e., the examinee) may be provided.

Here, in the template, a cluster name of the examinee, an illustration of the cluster, a one-line description expressing the cluster, a description of a naming reason for the cluster name, the examinee's position and description in a big data map corresponding to the examinee's age and gender, a description of a percentile of body composition of the examinee and a histogram description, and the like may be provided.

In this case, the service provider server 130 or the body composition data analysis application may also assign a specific name to each assigned cluster.

In this case, the service provider server 130 or the body composition data analysis application may also respectively provide illustrations corresponding to the assigned specific names.

In this case, the service provider server 130 or the body composition data analysis application may also provide position information of the user on the big data in relation to the assigned cluster.

In addition, when the service provider server 130 analyzes the user's body composition data and provides the cluster that is the group of similar body composition, to the user terminal 120 or the user terminal 120 analyzes the user's body composition data by the execution of the body composition data analysis application, assigns the cluster that is the group of the similar body composition, and displays the cluster on the display screen, the description for the reason for naming the name assigned to each cluster may be provided.

In this case, the service provider server 130 or the body composition data analysis application may provide information about that the cluster assigned to the user is a cluster corresponding to what percentage (%) of all examinees.

In this case, the service provider server 130 or the body composition data analysis application may also provide the percentile graph of the user on the big data.

In this case, the service provider server 130 or the body composition data analysis application may also provide an image storage function in a form of a card in which an illustration and a name thereof are combined with each other.

In addition, in analyzing the user's body composition data by the service provider server 130 or the body composition data analysis application installed in the user terminal 120, the body composition big data of at least one group among the same country, gender, and age as those of the user (i.e., the examinee) may be extracted to generate a big data map, and then analysis is performed on how much respective levels of at least one of obesity, muscle mass amount, and sarcopenia are illustrated in the group according to which coordinates the body composition data of the user (i.e., the examinee) is positioned in the generated body composition big data map.

In addition, in analyzing the user's body composition data and assigning the cluster, which is the group of similar body composition, by the service provider server 130 or the body composition data analysis application installed in the user terminal 120, a predetermined section of a statistically significant Body Mass Index (BMI) may be divided into a plurality of stages on the body composition big data for each user's gender/age by country, a predetermined portion of a Percentage Body Fat (PBF) from the total body composition big data included in the divided BMI band may be further divided into a plurality of regions, a cluster classification map that is changed depending on data parameters of each gender and each age group and has continuity may be generated, a map to be matched through age/gender information of the user who has completed a body composition test may be retrieved from a database (DB) to find a percentile position of each body composition of weight, height, body fat mass, and skeletal muscle mass and locate the percentile position on the map, and then the cluster may be assigned by a method of assigning one of a plurality of clusters on the basis of a unique address of a coordinate region to which a user (i.e., an examinee) belongs.

In this case, a section, from BMI 10 to BMI 42, statistically significant on the body composition big data for each user's gender/age by country may be divided into 60 stages.

In this case, an upper 1% to 99% of the PBF among the total body composition big data included in the divided BMI band may be further divided into nine regions by drawing lines.

The above content will be described later while describing the user clustering and analysis method according to the present disclosure.

Then, hereinafter, the user clustering and analysis method based on the user clustering and analysis system using the body composition big data according to the present disclosure having the above configuration will be described.

Figure 3:
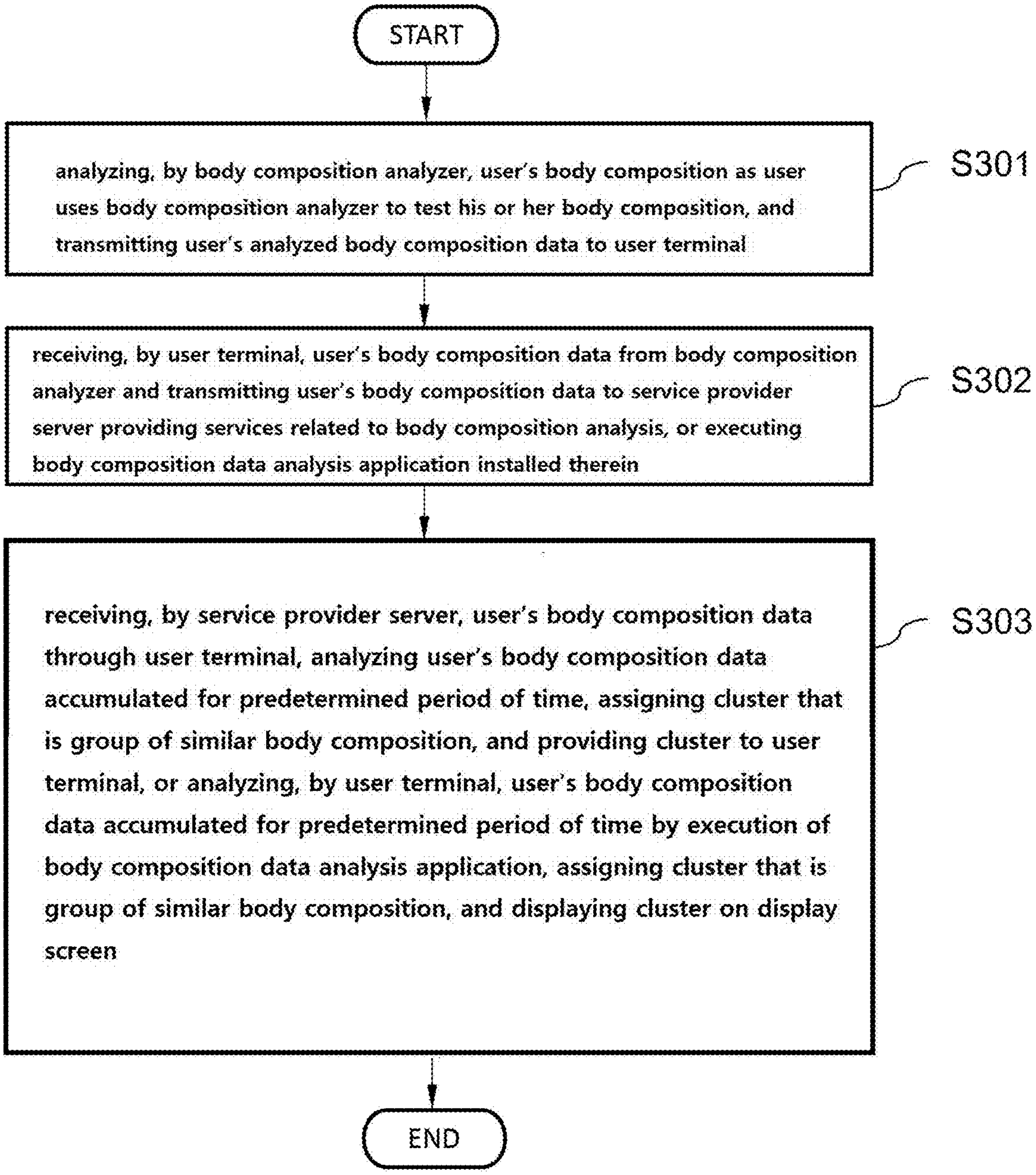
FIG. 3 is a flowchart illustrating an execution process of the user clustering and analysis method using the body composition big data according to the present disclosure.

FIG. 3 is a flowchart illustrating an execution process of the user clustering and analysis method using the body composition big data according to the exemplary embodiment of the present disclosure.

Referring to FIG. 3, first, in the user clustering and analysis method using the body composition big data, in step S301, a body composition analyzer 110 analyzes a user's body composition as the user uses the body composition analyzer 110 to test his or her body composition, and transmits the user's analyzed body composition data to a user terminal 120.

Accordingly, in step S302, the user terminal 120 receives the user's body composition data from the body composition analyzer 110 and transmits the user's body composition data to the service provider server 130 providing services related to the body composition analysis, or executes the body composition data analysis application installed therein.

Then, in step S303, the service provider server 130 receives the user's body composition data through the user terminal 120, analyzes the user's body composition data accumulated for a predetermined period of time, assigns a cluster that is a group of similar body composition, and provides the cluster to the user terminal 120, or the user terminal 120 analyzes the user's body composition data accumulated for the predetermined period of time by execution of the body composition data analysis application, assigns the cluster that is the group of the similar body composition, and displays the cluster on the display screen. Here, as described above, as for which one method to use between the method of analyzing the user's body composition data and assigning the clusters by the service provider server 130 and the method of analyzing the user's body composition data and assigning the clusters by way of executing the body composition data analysis application installed in the user terminal 120, each user may choose one of the methods according to his or her certain condition or situation. For example, when a user only needs to obtain a certain amount of information related to the analysis of the user's body composition data and the assignment of clusters, the method of analyzing the user's body composition data and assigning the clusters by way of executing the body composition data analysis application installed in the user terminal 120 may be used, and when the user desires more in-depth analysis and detailed information related to the user's body composition data analysis and the assignment of clusters, the method of analyzing the user's body composition data and assigning the clusters by the service provider server 130 may be used.

Here, in addition, the service provider server 130 or the body composition data analysis application of the user terminal 120 that analyzes the body composition data of the user (i.e., the examinee) and assigns the cluster will be described in more detail.

In the human body, a body weight, a height, a body fat percentage, and skeletal muscle mass are constantly changing, typically depending on gender and age. Currently, various institutions at home and abroad define obesity on the basis of the same fixed BMI, regardless of the age and gender, and the analysis of health and obesity in this way is a result of not considering social, cultural, and nutritional variables.

A server 130 of a service provider (e.g., InBody Co., Ltd.) in the user clustering and analysis system using the body composition big data of the present disclosure may access body composition big data having nearly 100 million records of users around the world, and thus, more rigorous body composition analysis may be conducted by using the statistical big data according to each group.

Figure 4:
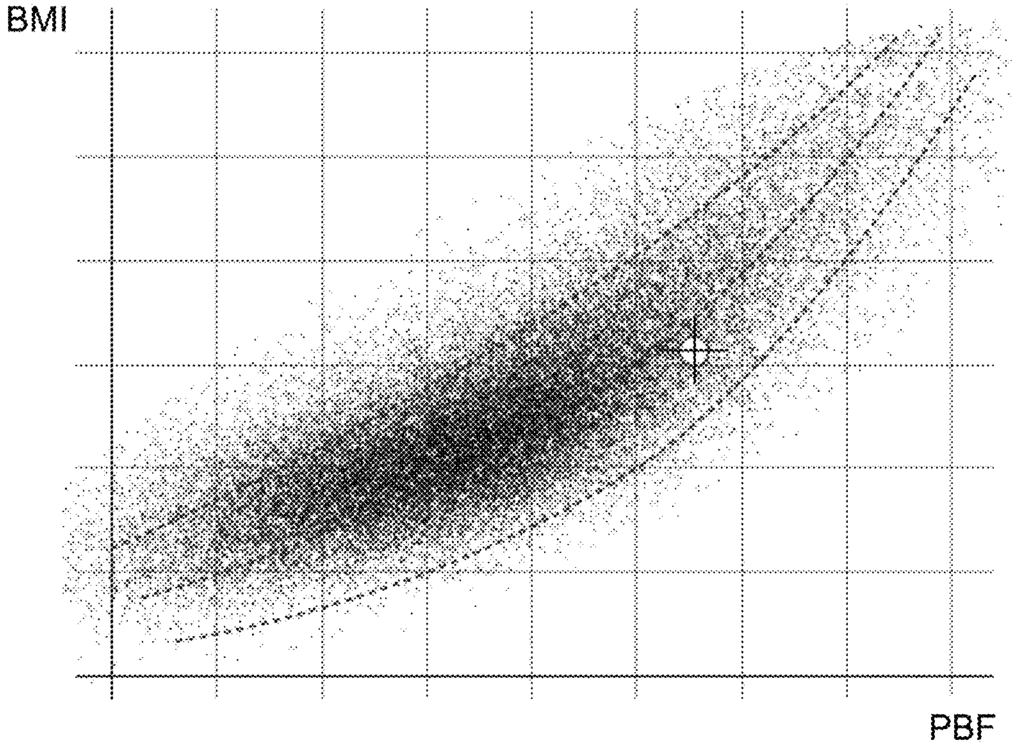
FIG. 4 is a view illustrating generation of a big data map by extracting the body composition big data of the same group as an examinee.

First, a big data map is generated as shown in FIG. 4 by extracting body composition big data of the same group (i.e., the same country, gender, and age as those of an examinee).

In this case, body composition of each user who uses the body composition analyzer (e.g., the body composition analyzer of InBody Co. Ltd.) in the past is expressed as a single point on the big data map without personal labeling.

Thereafter, according to coordinates at which the body composition data of the examinee is positioned in the generated body composition big data map, analysis is performed on how much respective levels of obesity, muscle mass amount, and sarcopenia are illustrated in the group. FIG. 4 is an example of a big data map of 25-year-old Korean females, and shows an overview that a body shape map with an x-axis as PBF and a y-axis as BMI is generated with the body composition big data of the 25-year-old female group to which an examinee belongs and the body composition is analyzed with the body composition coordinates of the examinee.

Next, assigning a cluster will be described.

First, a section, from BMI 10 to BMI 42, statistically significant on the body composition big data for each user's gender/age by country is divided into 60 stages.

Figure 5:
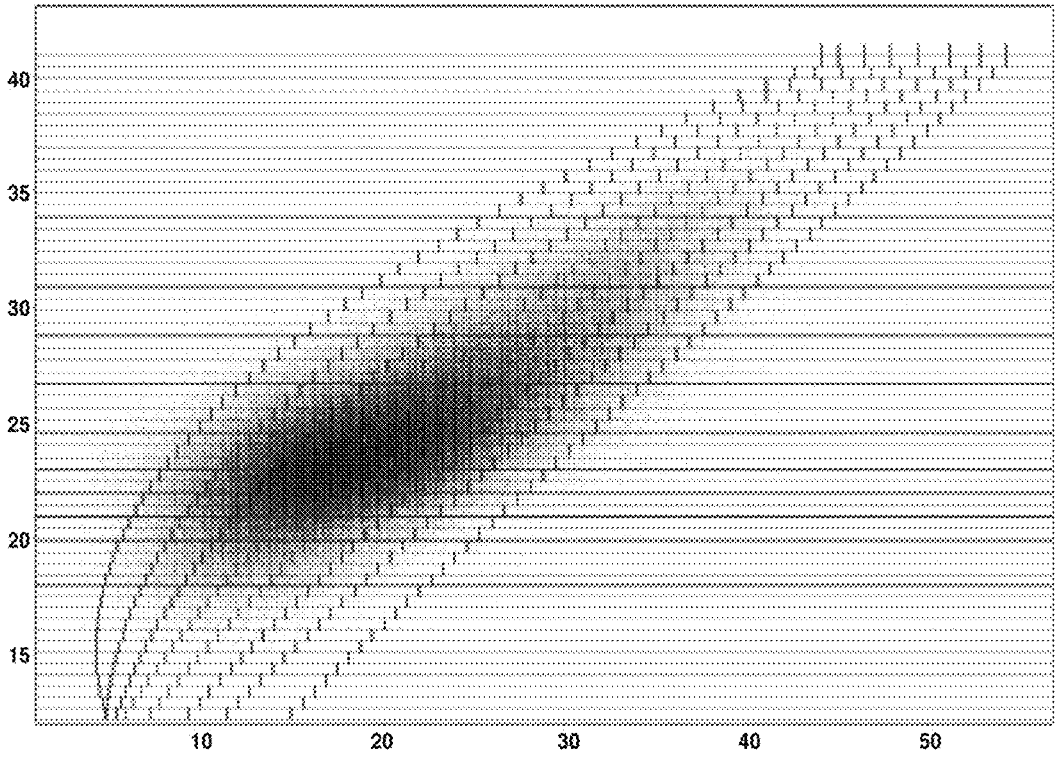
FIG. 5 is a view illustrating that a total of 540 coordinate regions each having a unique address are generated on one age/gender map.

Thereafter, the upper 1% to 99% of the PBF among the total body composition big data included in the divided BMI band is further divided into nine regions by drawing lines. Accordingly, as shown in FIG. 5, a total of 540 coordinate regions are generated on one age/gender map, and each coordinate region has a unique address.

Figure 6:
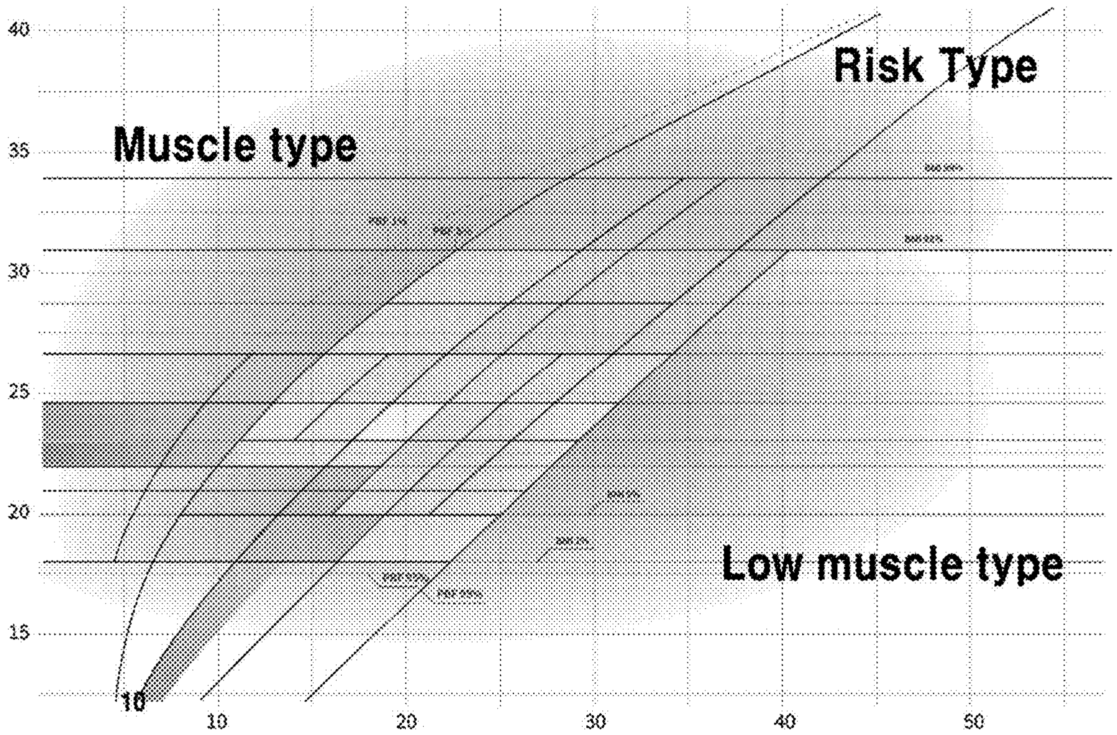
FIG. 6 is a view illustrating that each of a plurality of coordinate regions shown in FIG. 5 belongs to one of 50 clusters according to a position thereof.

In this case, as shown in FIG. 6, each coordinate region belongs to one of 50 clusters according to a position thereof. Here, each coordinate region is clustered once more, and one of the final clusters is assigned. FIGS. 5 and 6 are examples of a big data map of 25-year-old Korean males.

A cluster classification map is constantly changed depending on data parameters of each gender and each age group, and in this regard, the service provider server 130 (e.g., the server of InBody Co. Ltd.) generates an independent and continuous cluster classification map.

Thereafter, a map to be matched through age/gender information of the user who has completed an InBody test is retrieved from a DB. In addition, a percentile position of each body composition of weight, height, body fat mass, and skeletal muscle mass is found and placed on the map.

Then, one of 50 clusters is assigned at the time of first test on the basis of a unique address of a coordinate region to which an examinee belongs.

Figure 7:
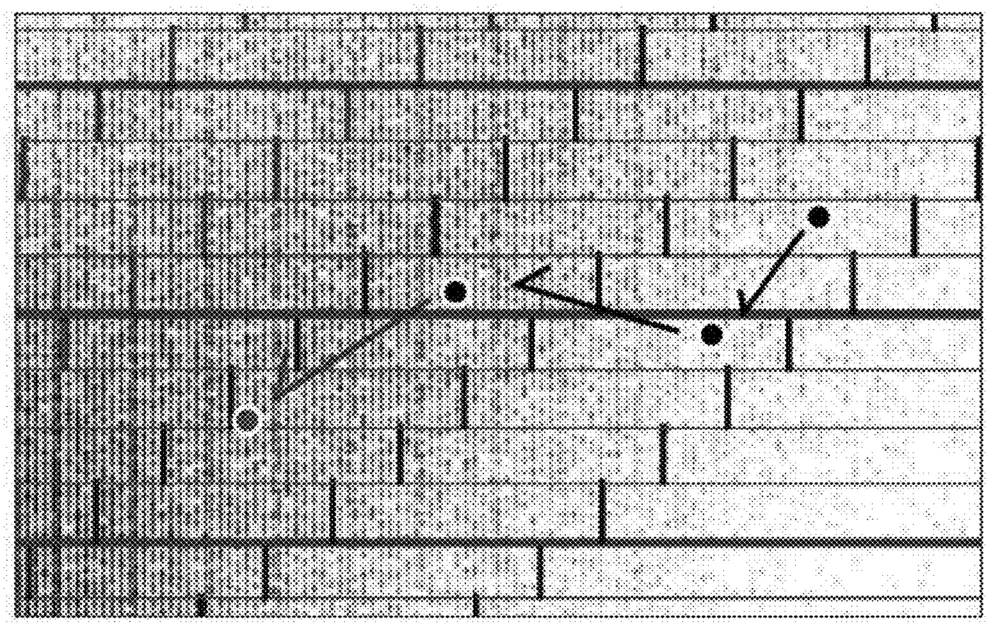
FIG. 7 is a view illustrating an outline of identifying a movement path of body composition of a user who has undergone a plurality of body composition tests for one month.
Figure 8:
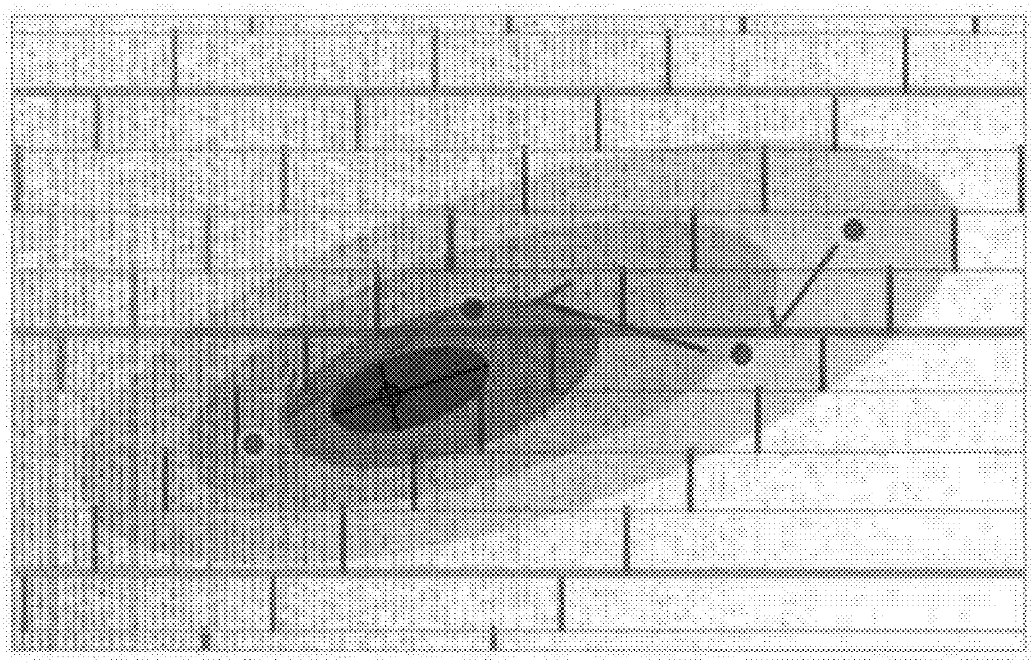
FIG. 8 is a view illustrating an outline of defining a final cluster for a corresponding month by giving a weight for each test period.

Thereafter, as shown in FIG. 7, a movement path of the body composition of the user who has undergone a plurality of body composition tests for one month is identified, and as shown in FIG. 8, a final cluster for a corresponding month is defined and assigned to the corresponding user (i.e., the examinee) by assigning a weight for each test period.

Meanwhile, in step S303, when the service provider server 130 analyzes the user's body composition data, assigns the cluster that is the group of the similar body composition, and provides the cluster to the user terminal 120 or the user terminal 120 analyzes the user's body composition data by the execution of the body composition data analysis application, assigns the cluster that is the group of the similar body composition, and displays the cluster on the display screen, a description of the assigned cluster may be provided.

Figure 9:
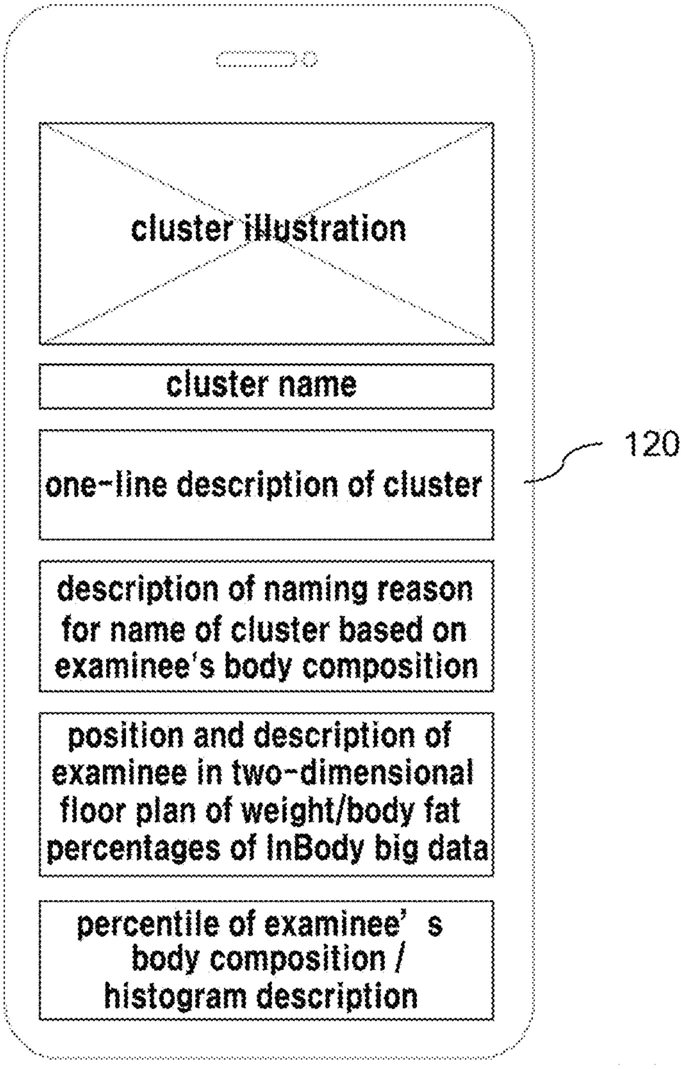
FIG. 9 is a view illustrating that a description according to a template of the cluster, the template being set in advance in response to the cluster assigned to the user (i.e., the examinee), is provided.

In this case, in providing the description of the assigned cluster, as shown in FIG. 9, a description according to a cluster template that is set in advance in response to the cluster assigned to the user (i.e., the examinee) may be provided.

Here, in the template, a cluster name of the examinee, an illustration of the cluster, a one-line description expressing the cluster, a description of a naming reason for the cluster name, a position and description of the examinee in a big data map (i.e., a two-dimensional floor plan of weight/body fat percentages of the big data) corresponding to the age and gender of the examinee, a description of a percentile of the body composition of the examinee and a histogram description, and the like may be provided.

Figure 10:
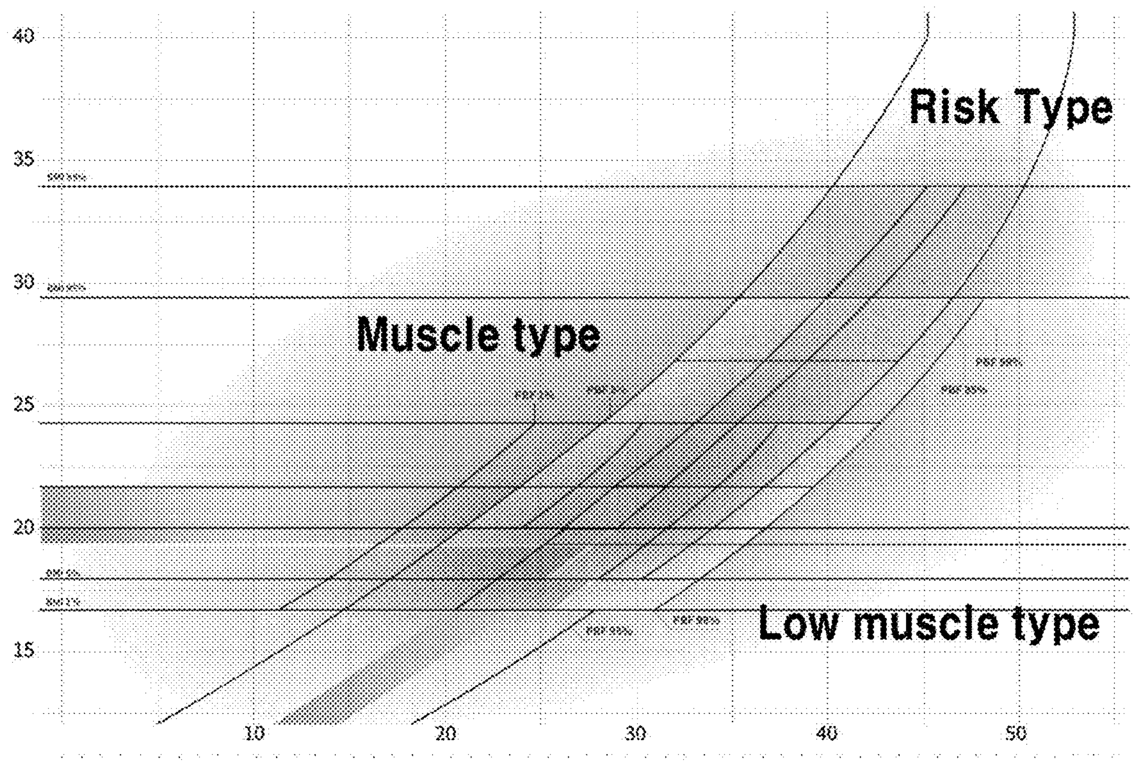
FIG. 10 is a view illustrating that each cluster of a cluster map according to each age and gender has a unique cluster name.

In this case, the service provider server or the body composition data analysis application may also assign a specific name to each assigned cluster. That is, as shown in FIG. 10, each cluster in the cluster map according to each age and gender may have a unique cluster name. The name is composed of Korean words or sentences, representing the body composition of the examinees gathered in the cluster, and may be expressed in direct expressions or analogies.

Here, even when the same cluster address is present, a cluster name may have a subdivided structure according to age/gender.

Figure 11:
FIG. 11 is a view illustrating cluster names that are differently expressed according to age and genders

For example, in a case of a cluster address of "L3", when an examinee is a female in her 20s, the examinee is expressed as a cluster name of "Rapunzel, a housekeeper" as shown in FIG. 11. However, for a female in her 50s, a cluster name may be expressed as "It's dangerous outside a blanket", and for a male in his 30s, a cluster name may be expressed as a "Indoor white hacker", and for a male in his 60s, a cluster name may be expressed as "Five meter radius of action".

Figure 12:
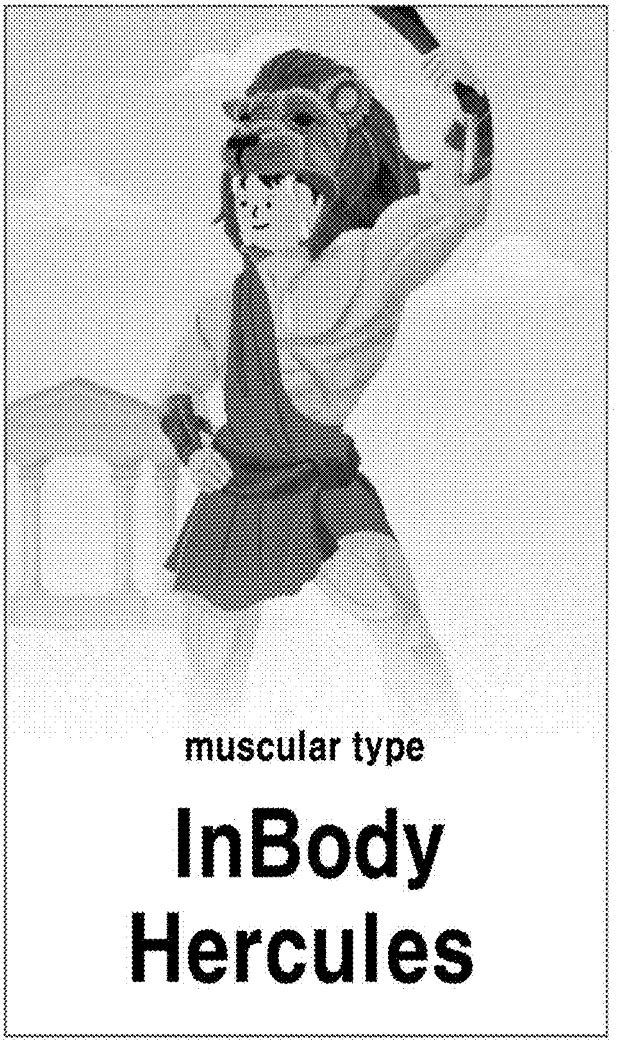
FIG. 12 is a view illustrating that a cluster name is assigned differently depending on the age and gender, and that each cluster name has a unique cluster illustration.

In this case, the service provider server 130 or the body composition data analysis application may also respectively provide illustrations corresponding to the assigned specific names. That is, each cluster address has a different cluster name according to age/gender corresponding to the different cluster name, and each name may have a unique cluster illustration as shown in FIG. 12.

Figure 13:
FIG. 13 is a view illustrating that a plurality of clusters is grouped into a plurality of groups, each group has a unique color, and the cluster name is compared to a person and expressed accordingly.

In addition, as shown in FIG. 13, a plurality of clusters (e.g., 105 clusters) is grouped into a plurality of groups, for example, 11 groups having respective types of "a muscle type", "a healthy type", "a thin type", "a normal type", "a stout type", "a skinny obesity type", "a mild obesity type", "an obesity type", "a severe obesity type", "a risk type", and "a low muscle type", and each group has its own unique color. All cluster illustrations are produced on the basis of the 11 group colors, and a method of expressing a cluster name compared to a person may be used, and the classification and body type of each of males and females may be reflected.

Figure 14:
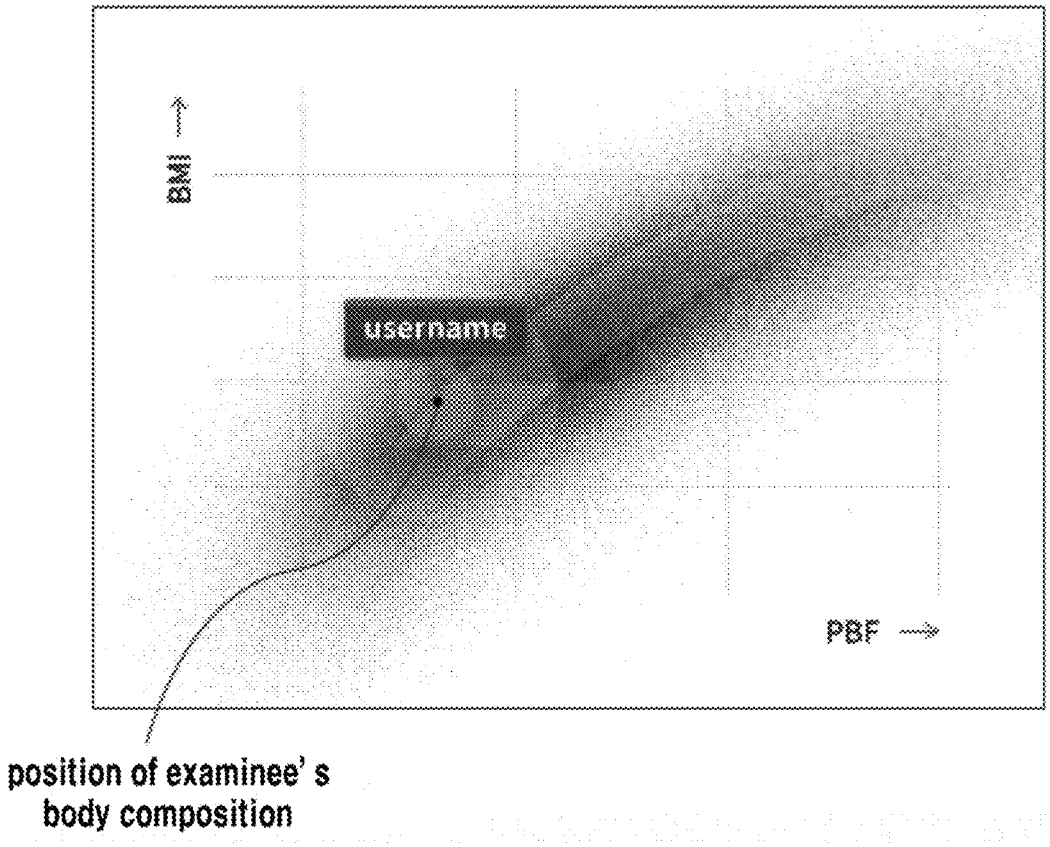
FIG. 14 is a view illustrating that distribution and mode bands of BMI and PBF for all users of the same sex/age as the examinee are displayed on a two-dimensional plane, and then positions of examinee's body composition are displayed.

In this case, the service provider server 130 or the body composition data analysis application may also provide position information of a user on big data in relation to the assigned cluster. That is, as shown in FIG. 14, all users of the same "gender" and "age" as those of the examinee are distributed on a two-dimensional plane, BMI mode bands and PBF mode bands of statistics are displayed on the two-dimensional plane, and then, a body composition position of the examinee is displayed as shown in FIG. 14, thereby providing position information of the user (i.e., the examinee). This also allows the examinee to identify the examinee's position on the whole big data and to identify the position on the basis of the mode bands.

In addition, when the service provider server analyzes the user's body composition data and provides the cluster that is the group of the similar body composition to the user terminal or the user terminal 120 analyzes the user's body composition data by the execution of the body composition data analysis application, assigns the cluster that is the group of the similar body composition, and displays the cluster on the display screen, the description for the reason for naming the name assigned to each cluster may be provided. In this regard, as described above, the user's (i.e., the examinee) gender and age are reflected (i.e., considered) to give the cluster name suitable for the user's gender and age, and a description therefor is provided. For example, a male in his 60s may be assigned a cluster name of "An active radius is five meters". A reason for giving such a name is that in a case of males in their 60s, on average, the males have relatively lower activity levels compared to young adults in their 20s and 40s, so the cluster name is assigned by reflecting (i.e., considering) such a situation, thereby the description is provided.

Figure 15A:
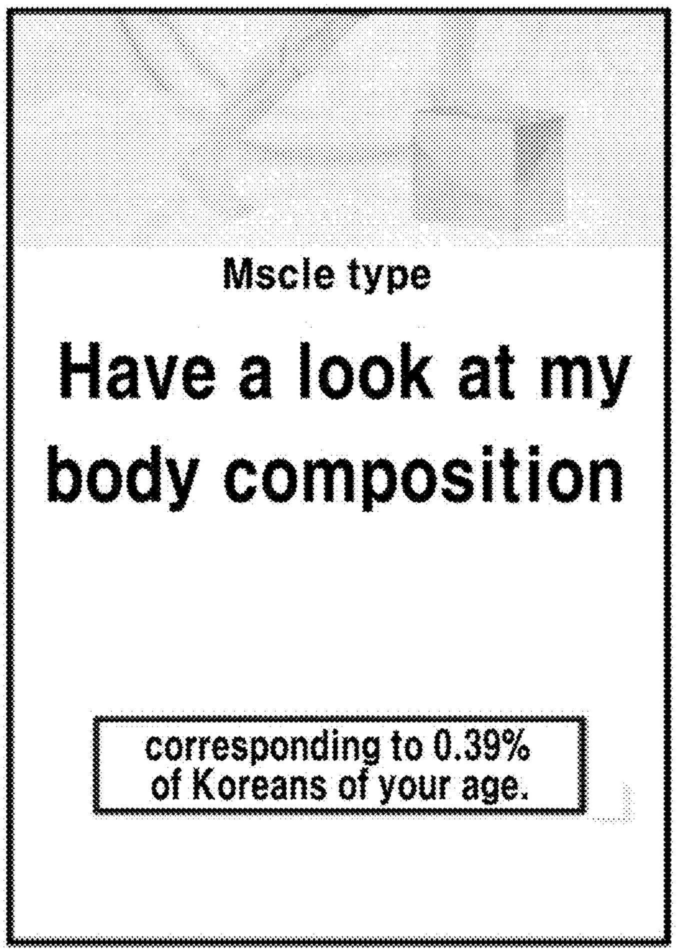
FIGS. 15A, 15B and 15C are views respectively illustrating a percentage of examinees in the cluster assigned to the user over all examinees, a body composition percentile graph of the examinee, and an image in a form of a card in which the illustration and a name thereof are combined with each other.

In this case, the service provider server 130 or the body composition data analysis application provides information about that the cluster assigned to the user is the cluster corresponding to what percentage (%) of all examinees. That is, as shown in FIG. 15A, a cluster population ratio is indicated under each cluster name, and a calculation equation is as follows:

(The number of users belonging to an examinee's cluster (n people)/The number of users with the same age and gender of the examinee (n people))*100

Figure 15B:
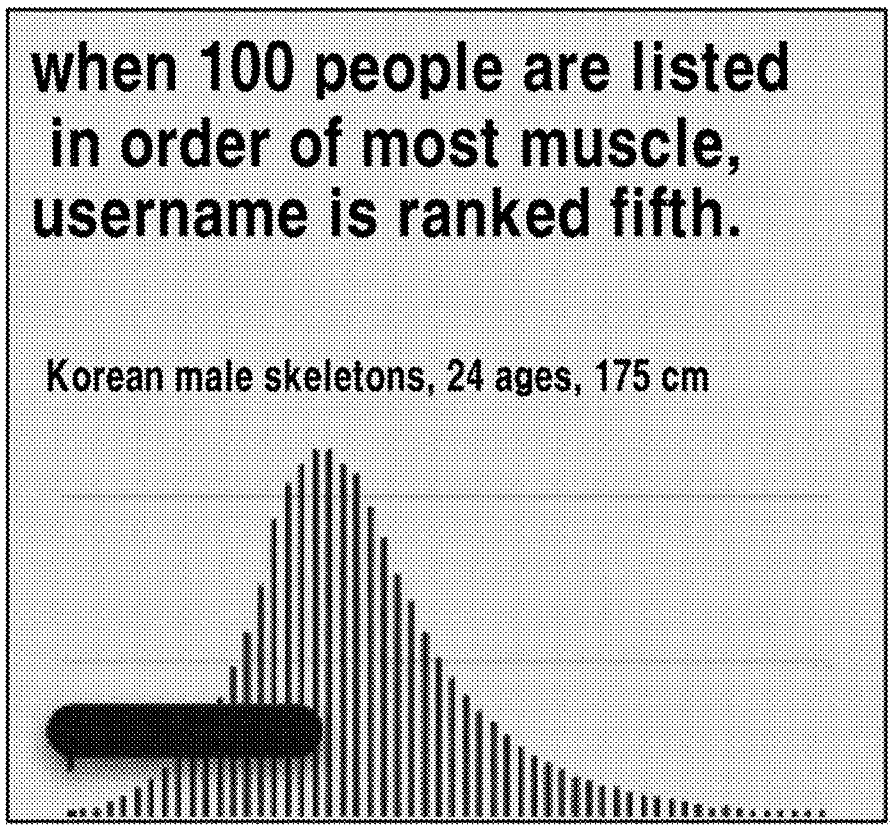

In this case, the service provider server 130 or the body composition data analysis application may also provide the percentile graph of the user on the big data. That is, as shown in FIG. 15B, the body composition percentile of the examinee among all other users of the same age and gender as those of the user (the examinee) is provided, and the histogram as illustrated with a format of an X-axis as body composition data and a Y-axis as the number of users is provided.

Figure 15C:
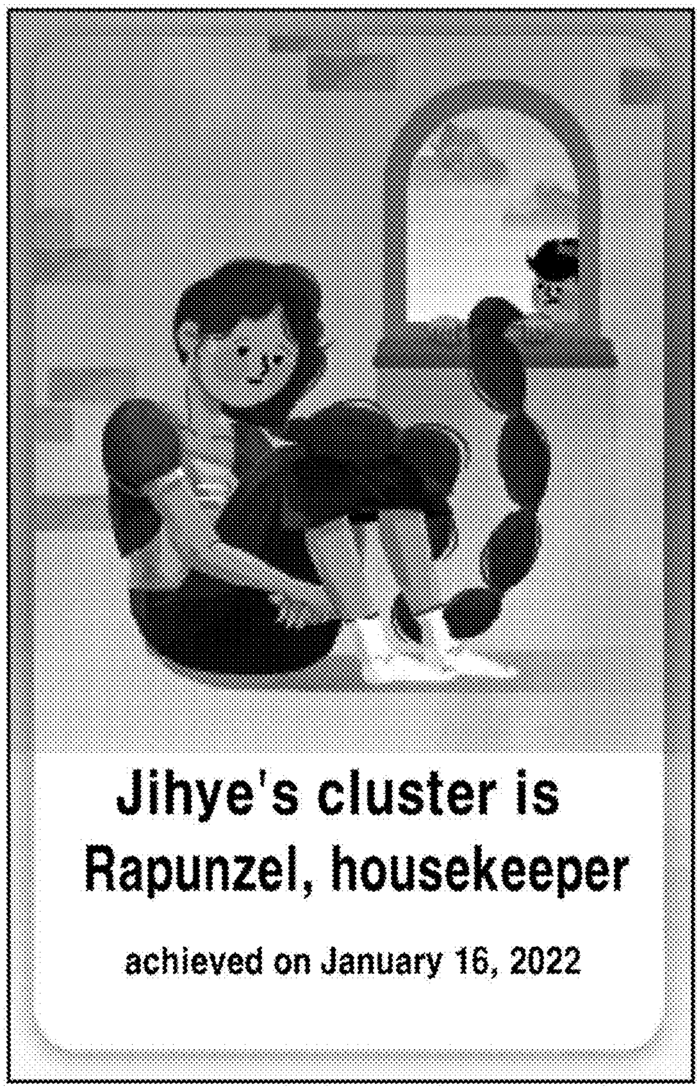

In this case, the service provider server 130 or the body composition data analysis application may also provide the image storage function in the form of the card in which the illustration and the name are combined with each other. That is, as shown in FIG. 15C, all users may respectively store their own clusters as a square PNG image file, and the image may be composed of the illustration and name of the cluster, an examinee's health app nickname, and a cluster card acquisition time.

In addition, in step S303, in analyzing the user's body composition data by the service provider server 130 or the body composition data analysis application installed in the user terminal 120, the body composition big data of at least one group among the same country, gender, and age as those of the user (i.e., the examinee) may be extracted to generate the big data map, and then the analysis is performed on how much respective levels of at least one of obesity, muscle mass amount, and sarcopenia are illustrated in the group according to which coordinates the body composition data of the user (i.e., the examinee) is positioned in the generated body composition big data map. This is the same as described above.

In addition, in step S303 of analyzing the user's body composition data and assigning the cluster, which is the group of similar body composition, by the service provider server 130 or the body composition data analysis application installed in the user terminal 120, the predetermined section of the statistically significant Body Mass Index (BMI) may be divided into the plurality of stages on the body composition big data for each user's gender/age by country, the predetermined portion of the Percentage Body Fat (PBF) from the total body composition big data included in the divided BMI band may be further divided into the plurality of regions, a cluster classification map that is changed depending on the data parameters of each gender and each age group and has the continuity may be generated, the map to be matched through the age/gender information of the user who has completed the body composition test may be retrieved from the database (DB) to find the percentile position of each body composition of weight, height, body fat mass, and skeletal muscle mass and locate the percentile position on the map, and then the cluster may be assigned by a method of assigning one of the plurality of clusters on the basis of the unique address of the coordinate region to which the user (i.e., the examinee) belongs.

In this case, the section, from BMI 10 to BMI 42, statistically significant on the body composition big data for each user's gender/age by country, may be divided into 60 stages.

In this case, the upper 1% to 99% of the PBF among the total body composition big data included in the divided BMI band may be further divided into nine regions by drawing the lines.

As described above, in the user clustering and analysis method and the system thereof using the body composition big data according to the present disclosure, there is the advantage in that the more improved body composition analysis services may be provided to the user by providing the detailed explanation of the user's body composition test results through the artificial intelligence natural language processing deep learning enabling the services as if a health trainer were explaining the test results in detail whenever the user examines his or her body composition by using a body composition analyzer.

As above, the present disclosure has been described in detail through the preferred exemplary embodiments, but the present disclosure is not limited thereto, and it is apparent to those skilled in the art that various changes and applications may be made within the scope of the present disclosure without departing from the technical spirit of the present disclosure.

Accordingly, the true protection scope of the present disclosure should be construed by the following claims, and all technical ideas within the scope equivalent thereto should be construed as being included in the scope of the present disclosure.

What is claimed is:

1. A user clustering and analysis method using body composition big data, the method comprising:
 - analyzing, by a body composition analyzer comprising a sensor unit provided with an electrode sensor and an automatic zero-point compensation load cell, and a handle unit provided with a pair of thumb electrodes for contacting both thumbs of a user, a body composition of the user as the user uses the body composition analyzer;
 - transmitting analyzed body composition data of the user to a user terminal;
 - receiving, by the user terminal, the analyzed body composition data from the body composition analyzer;
 - analyzing the analyzed body composition data accumulated for a predetermined period of time; and
 - assigning a cluster that is a group of similar body composition by:
   - generating a big data map by extracting body composition big data corresponding to a country, a gender and an age of the user from entire body composition big data,
   - dividing a Body Mass Index (BMI) section into a plurality of stages on the big data map,
   - dividing a Percentage Body Fat (PBF) from the big data map included in each divided BMI stage into a plurality of regions to generate a cluster classification map comprising a plurality of coordinate regions each having a unique address, wherein each coordinate region is mapped to one of a plurality of clusters,
   - retrieving the cluster classification map corresponding to a gender and an age of the user,
   - determining a coordinate region of the plurality of coordinate regions to which the user belongs based on the analyzed body composition data, and
   - assigning the cluster mapped to the coordinate region to the user; and
 - displaying, on a display screen, based on the cluster being assigned, a cluster template including a position of the user on the big data map, a cluster name and an illustration corresponding to the cluster assigned to the user, wherein the cluster template is set in advance in response to the cluster, wherein the cluster name is assigned differently depending on the age and the gender of the user even when a same cluster address is present,
 - wherein the position of the user on the big data map included in the cluster template is displayed by:
   - distributing all users having the gender and the age of the user on the big data map having BMI and PBF as axes;
   - displaying BMI mode bands and PBF mode bands on the big data map, and
   - providing position information of the user by displaying the analyzed body composition data of the user on the big data map.

2. The method of claim 1, further comprising:
 - displaying, on the display screen, the cluster and a description of the cluster.

3. The method of claim 2, wherein the description of the cluster comprises: the cluster name, the illustration of the cluster, a naming reason for the cluster name, and a histogram.

4. The method of claim 1, wherein the cluster classification map depends on data parameters of each gender and each age group, and is determined differently for the each gender and the each age group.

5. The method of claim 4, wherein the cluster is assigned differently when the gender and the age are different even when the unique address is identical, based on the cluster classification map being determined differently for the each gender and the each age group.

6. A user clustering and analysis system using body composition big data, the system comprising:
 - a body composition analyzer comprising:
   - a sensor unit provided with an electrode sensor and an automatic zero-point compensation load cell, and
   - a handle unit provided with a pair of thumb electrodes for contacting both thumbs of a user;
 - wherein the body composition analyzer is configured to analyze a body composition of the user as the user uses the body composition analyzer, and transmit analyzed body composition data of the user to a user terminal;
 - the user terminal configured to receive the analyzed body composition data from the body composition analyzer; and
 - a service provider server configured to (i) analyze the analyzed body composition data accumulated for a predetermined period of time, (ii) assign a cluster that is a group of similar body composition by:
   - generating a big data map by extracting body composition big data corresponding to a country, a gender, and an age of the user from entire body composition big data,
   - dividing a Body Mass Index (BMI) section into a plurality of stages on the big data map,
   - dividing a Percentage Body Fat (PBF) from the big data map included in each divided BMI stage into a plurality of regions to generate a cluster classification map comprising a plurality of coordinate regions each having a unique address, wherein each coordinate region is mapped to one of a plurality of clusters,
   - retrieving the cluster classification map corresponding to the gender and the age of the user,
   - determining a coordinate region of the plurality of coordinate regions to which the user belongs based on the analyzed body composition data, and
   - assigning the cluster mapped to the coordinate region to the user, and
 - (iii) provide the cluster to the user terminal; and
 - wherein the user terminal is further configured to:
   - display, on a display screen of the user terminal, based on the cluster being assigned, a cluster template including a position of the user on the big data map, a cluster name and an illustration corresponding to the cluster assigned to the user, wherein the cluster template is set in advance in response to the cluster, wherein the cluster name is assigned differently depending on the age and the gender of the user even when a same cluster address is present,
   - wherein the position of the user on the big data map included in the cluster template is displayed by:
     - distributing all users having the gender and the age of the user on the big data map having BMI and PBF as axes, displaying BMI mode bands and PBF mode bands on the big data map, and providing position information of the user by displaying the analyzed body composition data of the user on the big data map.

7. The system of claim 6, wherein the user terminal is further configured to:

display, on the display screen, the cluster and a description of the cluster.

8. The system of claim 7, wherein the description of the cluster comprises: the cluster name, the illustration of the cluster, a naming reason for the cluster name, and a histogram.

9. The system of claim 6, wherein the cluster classification map depends on data parameters of each gender and each age group, and is determined differently for the each gender and the each age group.

10. The system of claim 9, wherein the cluster is assigned differently when the gender and the age are different even when the unique address is identical, based on the cluster classification map being determined differently for the each gender and the each age group.

* * * * *